United States Patent [19]

Talwar et al.

[11] Patent Number: 4,945,087

[45] Date of Patent: Jul. 31, 1990

[54] TASTE MASKING OF THYMOL

[75] Inventors: Anil K. Talwar, Long Valley; Edward J. Carlin, Secaucus, both of N.J.

[73] Assignee: Warner-Lambert Company, Morris Plains, N.J.

[21] Appl. No.: 175,568

[22] Filed: Mar. 31, 1988

[51] Int. Cl.$^5$ ............... A61K 7/16; A61K 7/28/7/22
[52] U.S. Cl. ........................ 514/60; 424/49; 514/901; 514/974
[58] Field of Search .................. 514/60, 974, 901; 424/49

[56] References Cited

U.S. PATENT DOCUMENTS

| | | | |
|---|---|---|---|
| 1,484,415 | 2/1920 | Shepherd | 424/49 |
| 4,150,151 | 4/1979 | Pader et al. | 424/49 |
| 4,466,954 | 8/1984 | Ichikawa et al. | 424/49 |
| 4,726,943 | 2/1988 | Klueppel et al. | 424/49 |
| 4,774,076 | 9/1988 | Gomi et al. | 424/49 |

FOREIGN PATENT DOCUMENTS 22035084  6/1980  United Kingdom .

*Primary Examiner*—Ronald W. Griffin
*Attorney, Agent, or Firm*—Carl W. Battle; Craig Bell; Henry C. Jeanette

[57] ABSTRACT

A composition or a final product containing thymol in which the unpleasant, medicinal, or harsh taste of thymol has been masked is disclosed. The taste masking is accomplished utilizing effective amounts of a sugar alcohol, or a mixture of sugar alcohols, and anethole.

25 Claims, No Drawings

4,945,087

TASTE MASKING OF THYMOL

FIELD

This invention is directed to compositions containing thymol in which the medicinal taste of thymol is masked by the presence of a sugar alcohol, or mixtures of sugar alcohols, and anethole.

BACKGROUND

Thymol is a well known essential oil which is utilized for its antimicrobial activity in a variety of preparations. In particular, thymol can be utilized in oral hygiene preparations, such as mouth rinses, in sufficient quantities to provide desired beneficial therapeutic effects. Unfortunately, while thymol provides beneficial therapeutic effects, it also provides the consumer with a flavor perception that can be described as unpleasant, harsh or medicinal in taste. A welcome contribution to the art would be compositions containing thymol wherein the unpleasant, harsh or medicinal taste of thymol has been effectively masked. Such taste masked compositions would provide the consumer with a pleasant, acceptable taste. Further, such taste masked compositions would accomplish their end result without resorting to flavoring agents in large quantities having bold flavor notes which may be inharmonious to the overall flavor perception desired in the final product. This invention provides such compositions whose thymol taste is effectively masked.

SUMMARY OF THE INVENTION

This invention provides a composition or a final product containing thymol in which the unpleasant, medicinal, or harsh taste of thymol has been masked by the presence of a sugar alcohol, or a mixture of sugar alcohols, and an effective amount of anethole. The sugar alcohol and the anethole are present in amounts below which the thymol taste is not effectively masked. The presence of the sugar alcohol and the anethole masks the unpleasant taste of the thymol leaving the consumer with a pleasant taste perception.

Thus, this invention provides a composition comprising thymol, an effective amount of a sugar alcohol or mixtures of sugar alcohols, and an effective amount of anethole. The ratio of the sugar alcohol to the thymol is within the range of about 2750:1 to about 200:1, and the ratio of the anethole to the thymol is within the range of about 0.1:1 to about 1.75 to 1. This combination of sugar alcohol and anethole in the composition effectively masks the unpleasant, harsh, and medicinal taste of thymol without the need for additional flavorants, such as for example spearmint, peppermint, and the like.

In another embodiment, this invention provides an oral hygiene composition comprising effective amounts of thymol, a sugar alcohol or mixture of sugar alcohols, anethole, and other essential oils in which the unpleasant taste of thymol is effectively masked. In particular, the composition comprises thymol, a sugar alcohol or mixtures of sugar alcohols and anethole in admixture with eucalyptol, menthol, benzoic acid, methyl salicylate, ethanol, and, optionally, a surfactant or mixture of surfactants.

Therefore, another embodiment of this invention provides an oral hygiene composition comprising:

(a) about 0.02 to about 0.1% by weight of thymol;
(b) about 20 to about 55% by weight of a sugar alcohol;
(c) about 0.01 to about 0.035% by weight of anethole;
(d) about 0.04 to about 0.12% by weight of eucalyptol;
(e) about 0.02 to about 0.07% by weight of menthol;
(f) about 0.05 to about 0.25% by weight of benzoic acid;
(g) about 0.02 to about 0.09% by weight of methyl salicylate;
(h) about 5 to about 35% by weight of ethanol; and
(i) optionally, about 0.05 to about 0.8% by weight of a surfactant;

wherein the unpleasant taste of said thymol is masked by said sugar alcohol and said anethole, and wherein said percents by weight are based on the total weight of the composition.

In yet another embodiment of this invention, there is provided a method for masking the taste of thymol in a composition or final product. The method comprises adding an effective amount of a sugar alcohol, or mixture of sugar alcohols, and an effective amount of anethole to the product. The ratio of the sugar alcohol to the thymol in the final product is within the range of about 2750:1 to about 200:1, and the ratio of the anethole to the thymol in the final product is within the range of about 0.1:1 to about 1.75:1.

DETAILED DESCRIPTION OF THE INVENTION

It will be appreciated by those skilled in the art that the threshold level perception of various types of flavoring agents is different from consumer to consumer; therefore, the level of anethole utilized in the compositions of this invention will either provide a pleasant tasting final composition with minimal to no perceived anethole flavor, or will provide a composition with a mild, pleasant, subtle anethole flavor. Of course, those skilled in the art will also appreciate that higher levels of anethole may be utilized to provide a stronger anethole flavor in accordance with individual taste preference.

In the compositions of this invention, the preferred ratio of sugar alcohol to thymol is from about 333:1 to about 1000:1, and most preferably 400:1 to about 533:1. Preferably, the ratio of anethole to thymol is about 0.2:1 to about 0.5:1 and most preferably about 0.25:1 to about 0.37:1.

Generally, the sugar alcohol will be present in amounts of about 20 to about 55% by weight, based on the weight of the total composition, with about 25 to about 50% by weight being preferred, and about 28 to about 32% being most preferred. Suitable amounts of anethole are usually in the range of about 0.01 to about 0.035% by weight, based on the weight of the total composition, with about 0.015 to about 0.025% by weight being preferred and about 0.018 to about 0.022% by weight being most preferred. In the compositions containing these amounts of sugar alcohol and anethole, the thymol is usually present in amounts of not more than about 0.1% by weight, based on the weight of the total composition, with about 0.02 to about 0.1% by weight being preferred, and about 0.05 to about 0.075% by weight being most preferred.

The sugar alcohols that are utilizable in the present invention are any of those known in the art which have effective sweetening capabilities. Generally, the sugar alcohols are selected from the group consisting of sorbitol, xylitol, mannitol, maltitol, hydrogenated starch hydrolysate, and mixtures thereof. Preferably, the sugar alcohol is sorbitol.

The compositions of this invention may, in addition to the thymol, include effective amounts of other essential oils such as those selected from the group consisting of eucalyptus, menthol, methyl salicylate, and the like, and mixtures thereof. Generally, the total amount of essential oils present in a composition, exclusive of the thymol, can be from about 0.05 to about 0.35% by weight, based on the weight of the composition, with about 0.12 to about 0.28% by weight being preferred. For example, the compositions, as stated above, can contain eucalyptol, menthol, and methyl salicylate. Preferably the eucalyptol is present in amounts of about 0.07 to about 0.11% being preferred and most preferably about 0.08 to about 0.10%; preferably menthol is present in amounts of about 0.03% to about 0.06% by weight and most preferably about 0.04 to about 0.05%; and preferably methyl salicylate is present in amounts of about 0.03 to about 0.08% by weight and most preferably about 0.04 to about 0.07%; said % by weight being based on the total composition. In addition to these essential oils, benzoic acid is preferably present in amounts of about 0.1 to about 0.2% by weight, based on the total composition and most preferably about 0.13 to about 0.18%.

Compositions or final products containing thymol, in which the taste of thymol is masked by the presence of the sugar alcohol and the anethole, include liquid oral preparations such as a mouthwash, spray or rinse. In such preparations the vehicle —i.e. the carrier for the ingredients of the mouthwash, such as the essential oils, and the like— is typically a water-alcohol mixture. Generally the ratio of water to alcohol is in the range of from about 1:1 to about 20:1, preferably about 3:1 to about 20:1 and most preferably about 3:1 to about 10:1 by weight. The total amount of water-alcohol mixture in a mouthwash preparation is typically in the range from about 50% to about 99.9% by weight of the composition. The pH value of such mouthwash preparations is generally from about 3.5 to about 8.0 and preferably from about 4 to about 7.5. A pH below 3.5 would be irritating to the oral cavity and soften tooth enamel. A pH greater than 8 would result in an unpleasant mouth feel.

Oral liquid preparations may also contain surface active agents —i.e. surfactants— in amounts up to about 5% and fluorine-providing compounds in amounts up to about 2% by weight of the preparation.

Surface active agents (surfactants) are organic materials which aid in the complete dispersion of the preparation throughout the oral cavity. The organic surface active material may be anionic, non-ionic, ampholytic, or cationic. Suitable anionic surfactants are water-soluble salts of higher fatty acid monoglyceride monosulfates, such as the sodium salt of the monosulfated monoglyceride of hydrogenated coconut oil fatty acids; higher alkyl sulfates, such as sodium lauryl sulfate; alkyl aryl sulfonates, such as sodium dodecyl benzene sulfonate; higher alkyl sulfonacetates; higher fatty acid esters of 1,2-dihydroxy propane sulfonates; and substantially saturated higher aliphatic acyl amides of lower aliphatic amino carboxylic acids such as those having 12 to 16 carbons at the fatty acid, alkyl or acyl radicals. Examples of the last mentioned amides are N-lauroyl sarcosine, and the sodium, potassium, and ethanolamide salts of N-lauroyl, N-myristyl or N-palmitoyl sarcosine.

The non-ionic surfactants employed are poly(oxyethylene)-poly(oxypropylene) block copolymers. Such copolymers are known commercially as poloxamers and are produced in a wide range of structures and molecular weights with varying contents of ethylene oxide and propylene oxide. The non-ionic poloxamers according to the invention are non-toxic and acceptable as direct food additives. They are stable and readily dispersible in aqueous systems and are compatible with a wide variety of formulating ingredients for oral preparations. These surfactants should have an HLB (Hydrophilic-Lipophilic Balance) of between about 10 and 30 and preferably between 10 and 25.

Thus, non-ionic surfactants useful in this invention include poloxamers:

| 105 | 188 | 284 |
| 108 | 215 | 288 |
| 123 | 217 | 334 |
| 124 | 234 | 335 |
| 183 | 235 | 338 |
| 184 | 237 | 407 |
| 185 | 238 | |

Generally these polymers should constitute from 0.2% to 2% by weight of total volume of liquid oral preparation (% w/v) and preferably from 0.5% to 1% w/v. A particularly preferred poloxamer is Poloxamer 407 having an HLB of about 22. Such a polymer is sold under the trademark Pluronic F-127 (BASF-WYANDOTTE).

Another class of non-ionic surfactants useful in this invention are ethoxylated hydrogenated castor oils. Such surfactants are prepared by hydrogenating castor oil and treating the so-formed product with from about 10 to 200 moles of ethylene glycol. They are designated as PEG (numeral) hydrogenated castor oil in accordance with the dictionary of the Cosmetics, Toiletries and Fragrance Association, 3rd Ed. wherein the numeral following PEG indicates the degree of ethoxylation, i.e. the number of moles of ethylene oxide added. Suitable PEG hydrogenated castor oils include PEG 16, 20, 25, 30, 40, 50, 60, 80, 100 and 200. The ethoxylated hydrogenated castor oils are used in the same concentrations as the above described poly(oxyethylene)-poly(oxypropylene) block copolymers.

Other non-ionic surface active agents which may be suitable include codensates of sorbitan esters of fatty acids with from 20 to 60 moles of ethylene oxide (e.g., "Tweens" a trademark of ICI United States, Inc.), and amphoteric agents such as quaternized imidazole derivatives.

Additional non-ionic surfactants which may be suitable are the condensation products of an alpha-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant surfactants are polymers having a molecular weight in the range of 400 to about 1600 and containing 40% to 80% by weight of ethylene oxide, with an alpha-olefin oxide to polyhydric alcohol mole ratio in the range of about 1:1 to 1:3.

Cationic surface active agents which may be suitable are molecules that carry a positive charge such as cetylpyridinium chloride.

Fluorine providing compounds may be present in the oral preparations of this invention. These compounds may be slightly water soluble or may be fully water soluble and are characterized by their ability to release fluoride ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid preparation such as a mouthwash, the fluorine providing compound is generally present in an amount sufficient to release up to about 0.15%, preferably about 0.001% to about 0.1% and most preferably from about 0.001% to about 0.05% fluoride by weight of the preparation.

If desired, auxiliary sweeteners may be utilized in the compositions of this invention. Those sweeteners which may be included are those well known in the art, including both natural and artificial sweeteners.

The sweetening agent (sweetener) used may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof. Without being limited to particular sweeteners, representative illustrations encompass:

A. Water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. Water-soluble artificial sweeteners such as the soluble saccharin salts, i.e. sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. Dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4--tetramethyl-3-thietanyl)-D-alaninamide hydrate, methyl esters of L-aspartyl-L-phenylglycerine and L-aspartyl-L-2,5,dihydrophenyl-glycine, L-aspartyl-2,5-dihydro-L-phenylalanine; L-aspartyl-L-(1-cyclohexyen)-alanine; and the like;

D. Water-soluble sweeteners derived from naturally occurring water-soluble sweeteners, such as a chlorinated derivative of ordinary sugar (sucrose), known, for example, under the product description of sucralose; and E. Protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.01% to about 40% by weight of the composition when using an easily extractable sweetener. The water-soluble sweeteners described in category A above, are usually used in amounts of about 5% to about 40% by weight, and preferably in amounts of about 10% to about 20% by weight of the final composition. Some of the sweeteners in category A (e.g., glycyrrhizin) may be used in amounts set forth for categories B-E below due to the sweeteners' known sweetening ability. In contrast, the sweeteners described in categories B-E are generally used in amounts of about 0.005% to about 5.0% by weight of the final composition with about 0.03% to about 2.5% by weight being usual and about 0.03 to about 0.4% by weight being preferred. These amounts may be used to achieve a desired level of sweetness independent from the flavor level achieved from any optional flavor oils used.

The use of the sugar alcohols and the anethole, as discussed above, results in the successful taste masking of the thymol taste. The compositions so masked have a pleasing taste, and, depending on the threshold level of perception of the consumer, may have a pleasing anethole flavor perception. Therefore, additional flavorants or flavors are not necessary; however, if desirable, additional flavorings (flavors) may be added.

The flavorings (flavoring agents) that may be used include those known to the skilled artisan, such as, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almonds. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, menthol, artificial vanilla, cinnamon derivatives, and various fruit flavors, whether employed individually or in admixture.

Flavorings such as aldehydes and esters including cinnamyl acetate, cinnamaldehyde, citral, diethylacetal, dihydrocarvyl acetate, eugenyl formate, p-methylanisole, and so forth may also be used. Generally any flavoring or food additive such as those described in *Chemicals Used in Food Processing*, pub 1274 by the National Academy of Sciences, pages 63–258 may be used.

Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.05% to about 2.0% by weight of the composition are useable with amounts of about 0.05% to about 1.5% being preferred.

The compositions of this invention may also contain coloring agents or colorants.

The coloring agents are used in amounts effective to produce the desired color. The coloring agents (colorants) useful in the present invention, include the pigments such as titanium dioxide, which may be incorporated in amounts of up to about 2% by weight of the composition, and preferably less than about 1% by weight. Colorants may also include natural food colors and dyes suitable for food, drug and cosmetic applications. These colorants are known as F.D. & C. dyes and lakes. The materials acceptable for the foregoing spectrum of use are preferably water-soluble, and include indigoid dye, known as F.D. & C. Blue No. 2, which is the disodium salt of 5,5-indigotindisulfonic acid. Similarly, the dye known as Green No. 1 comprises a triphenylmethane dye and is the monosodium salt of 4-[4-N-ethyl-p-sulfobenzylamino)diphenylmethylene]-[1-N-ethyl-N-p-sulfoniumbenzyl)-$\Delta^{2,5}$-cyclohexadienimine]. Additional examples include the yellow dye, known as D&C Yellow No. 10, and the dye known as F.D.& C. Green No. 3 which comprises a triphenylmethane dye. A full recitation of all F.D.& C. and D. & C. dyes and their corresponding chemical structures may be found in the Kirk-Othmer Encyclopedia of Chemical Technology, Volume 5, Pages 857-884, which text is accordingly incorporated herein by reference.

The oral compositions of this invention may also be substantially solid or pasty in character such as a dental cream, toothpaste, or a toothpowder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. For toothpaste and dental creams the water content is about 25% to 50% by weight.

In clear gels, a polishing agent of colloidal silica and alkali metal aluminosilicate complexes are preferred since they have refractive indicies close to the refractive indicies of gelling agent liquid systems commonly used in dentifrices.

In the oral preparation that are toothpastes, dental creams, or gels the liquid vehicle may comprise water, typically in an amount of about 10-90% by weight of the composition. Polyethylene glycol, propylene glycol, glycerin or mixtures thereof may also be present as humectants or binders in amounts of about 20-25% by weight. Particularly advantageous liquid ingredients comprise mixtures of water with polyethylene glycol or glycerin and propylene glycol. A gelling agent (thickening agent) including natural or synthetic gums such as sodium carboxymethylcellulose, hydroxyethyl cellulose, methyl cellulose and the like may be used, in the range of about 0.5-5% by weight. In a toothpaste, dental cream or gel, the liquids and solids are proportioned to form a creamy or gelled mass which is extrudable from a pressurized container or from a collapsible tube.

The toothpaste or gel may also contain a surface active agent which may be an anionic, nonionic or zwitterionic detergent (surfactant) in amounts of about 0.05-5% by weight. The anionic and nonionic surfactants that are suitable have already been discussed above.

Zwitterionic surface active agents include the betaines and sulfobetaines. Typical alkyl dimethyl betaines include decyl betaine or 2-(N-decyl-N,N-dimethylammonio) acetate, coco betaine, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like. These sulfobetaines are similar in structure to the betaines, but have a sulfonate group in place of the carboxylate group, and include alkylsulfobetaines, alkylamidosulfobetaines and alkylaminosulfobetaines.

In general, the compositions of this invention are prepared utilizing techniques well known to those skilled in the art. Thus, the liquid compositions may be prepared by mixing the alcohol soluble ingredients with ethanol, adding a quantity of water to the mixture thus obtained, and then blending or mixing in the water soluble ingredients. For example, in preparing one liter of a typical liquid oral composition, thymol, eucalyptol, menthol, methyl salicylate, anethole, surfactant, and benzoic acid are dissolved in and mixed with ethanol. To this resulting mixture a sufficient quantity of water is added, and then the auxiliary sweetener, water soluble colorants, buffers, and the like are blended in. Then additional water is added to make up one liter.

Those skilled in the art will appreciate that the total amount of all ingredients (components) used in the compositions of this invention equals 100% by weight of the total composition. Also, unless stated otherwise, all percents herein are percent by weight of the total composition.

The following examples are illustrative only and should not be construed as limiting the invention in any way. Those skilled in the art will appreciate that variations are possible which are within the spirit and scope of the appended claims.

In the examples that follow, the compositions were prepared by blending the thymol, eucalyptol, menthol, methyl salicylate, anethole, and surfactant with the ethanol. To the resulting mixture about 300 mL of water was mixed therewith, and then the remaining water soluble ingredients were added —e.g., the sodium saccharin, buffers (citric acid and sodium citrate), the colorants, and the like— and blended in. To this resulting mixture, enough water was added to make one liter of solution. Prior to taste evaluation, all compositions were aged a minimum of 5 days at room temperature.

EXAMPLES 1 AND 2

Examples 1 and 2, presented in Table I, represent compositions of this invention.

TABLE I

| Ingredient | EXAMPLES (g/L of Final Solution) | |
| --- | --- | --- |
|  | 1 | 2 |
| Thymol | 0.639 | 0.639 |
| Sorbitol | 300 | 300 |
| Anethole | 0.2 | 0.2 |
| Ethanol | 228 | 228 |
| Eucalyptol | 0.922 | — |
| Menthol | 0.425 | — |
| Benzoic Acid | 1.5 | 1.5 |
| Methyl Salicylate | 0.552 | — |
| Poloxamer 407 | 5 | 5 |
| Sodium Saccharin | 0.3 | 0.3 |
| Sodium Citrate | 0.3 | 0.3 |
| Citric Acid | 0.1 | 0.1 |
| Color | 0.004 | 0.004 |
| Water QS 1 Liter | — | — |

The flavor perceptions of the formulations in Examples 1 and 2 were as follows:

Example 1: some anethole taste; and

Example 2: slightly strong anethole taste but not thymol taste

These data demonstrate the effective taste masking of thymol.

EXAMPLES 3-11

Examples 3-11, set forth in Table II, represent formulations which are on-inventive and therefore serve as comparative examples.

Examples 3-11 had the same formulation as in Example 1 except the amounts of the sorbitol and anethole were varied. The amounts of the sorbitol and anethole for these examples are given in Table II as g/L of final solution.

The flavor perceptions of these comparative formulations are also given in Table II.

TABLE II

| Example | Sorbitol | Anethole | Comments |
| --- | --- | --- | --- |
| 3 | 300 | 0.05 | Thymol comes through |
| 4 | 300 | 0.5 | Unacceptably strong anethole |
| 5 | 0 | 0 | Thymol comes through |
| 6 | 0 | 0.2 | Slight thymol aftertaste |
| 7 | 300 | 0 | Thymol comes through |
| 8 | 100 | 0 | Thymol comes through |
| 9 | 500 | 0 | Thymol comes through |
| 10 | 0 | 0.3 | Too much anethole |
| 11 | 100 | 0.2 | Strong anethole, some thymol |

The data presented in Table II (non-inventive) in comparison to that of Table I (inventive) demonstrates that the sorbitol and anethole are needed within certain amounts in order to effectively and completely mask the taste of the thymol.

EXAMPLE 12

Example 12 is directed to a comparative, non-inventive composition similar to that of Example 2 except the formulation of Example 12 contained no sorbitol and no anethole. The formulation was found to have a very strong thymol taste.

The invention thus being described, it will be obvious that the same may be varied in many ways. Such variations are not to be regarded as a departure from the spirit and scope of the invention and all such modifications are intended to be included within the scope of the claims.

What is claimed is:

1. A composition comprising thymol, an effective amount of a sugar alcohol, and an effective amount of anethole wherein the ratio of said sugar alcohol to said thymol is within the range of about 2750:1 to about 200:1, and the ratio of said anethole to said thymol is within the range of about 0.1:1 to about 1.75 to 1, wherein the combination of said sugar alcohol and said anethole mask the unpleasant taste of said thymol.

2. The composition of claim 1 wherein said sugar alcohol is selected from the group consisting of sorbitol, xylitol, mannitol, maltitol, hydrogenated starch hydrolsate, and mixtures thereof.

3. The composition of claim 2 wherein said sugar alcohol is sorbitol.

4. The composition of claim 1 wherein said thymol is present in amounts of about 0.02 to about 0.1% by weight, said sugar alcohol is present in amounts of about 20 to about 55% by weight, and said anethole is present in amounts of about 0.01 to about 0.035% by weight, wherein said percents by weight are based on the total weight of the composition.

5. The composition of claim 4 wherein said sugar alcohol is present in amounts of about 25 to about 50% by weight, said anethole is present in amounts of about 0.015 to about 0.025% by weight, and said thymol is present in amounts of about 0.05 to about 0.075% by weight.

6. The composition of claim 4 wherein said sugar alcohol is present in amounts of about 28 to about 32% by weight, said anethole is present in amounts of about 0.018 to about 0.022% by weight, and said thymol is present in amounts of about 0.06 to about 0.07% by weight.

7. The composition of claim 4 wherein said sugar alcohol is selected from the group consisting of sorbitol, xylitol, mannitol, maltitol, hydrogenated starch hydrolysate, and mixtures thereof.

8. The composition of claim 7 wherein said sugar alcohol is sorbitol.

9. The composition of claim 5 wherein said sugar alcohol is sorbitol.

10. The composition of claim 6 wherein said sugar alcohol is sorbitol.

11. The composition of claim 1 comprising additional ingredients selected from the group consisting of about 0.04 to about 0.12% by weight eucalyptol, about 0.02 to about 0.07% by weight menthol, about 0.05 to about 0.25% by weight benzoic acid, about 0.02 to about 0.09% by weight methyl salicylate, about 5 to about 35% by weight ethanol, and mixtures thereof, said % by weight being based on the total weight of the composition.

12. An oral hygiene composition comprising
(a) about 0.02 to about 0.1% by weight of thymol;
(b) about 20 to about 55% by weight of a sugar alcohol;
(c) about 0.01 to about 0.035% by weight of anethole;
(d) about 0.04 to about 0.12% by weight of eucalyptol;
(e) about 0.02 to about 0.07% by weight of menthol;

(f) about 0.05 to about 0.25% by weight of benzoic acid;

(g) about 0.02 to about 0.09% by weight of methyl salicylate; and (h) about 5 to about 35% by weight of ethanol;

wherein the unpleasant taste of said thymol is masked by said sugar alcohol and said anethole, and wherein said percents by weight are based on the total weight of the composition.

13. The composition of claim 12 wherein said sugar alcohol is selected from the group consisting of sorbitol, xylitol, mannitol, maltitol, hydrogenated starch hydrolsate, and mixtures thereof.

14. The composition of claim 13 wherein said sugar alcohol is sorbitol.

15. The composition of claim 12 comprising additionally a surfactant selected from the group consisting of anionic, non-ionic, and cationic surractants 16. The composition of claim 15 wherein said surfactant is a non-ionic surfactant.

17. The composition of claim 16 wherein said surfactant is a poloxamer.

18. The composition of claim 17 wherein the sugar alcohol is selected from the group consisting of sorbitol, xylitol, mannitol, maltitol, hydrogenated starch hydrolysate, and mixtures thereof.

19. The composition of claim 18 wherein said sugar alcohol is sorbitol.

20. A method for masking the taste of thymol in a final product comprising adding an effective amount of a sugar alcohol and an effective amount of anethole to said product wherein the ratio of said sugar alcohol to said thymol is within the range of about 2750:1 to about 200:1, and the ratio of said anethole to said thymol is within the range of about 0.1:1 to about 1.75 to 1, wherein the combination of said sugar alcohol and said anethole mask the unpleasant taste of said thymol.

21. The method of claim 20 wherein the sugar alcohol is selected from the group consisting of sorbitol, xylitol, mannitol, maltitol, hydrogenated starch hydrolysate, and mixtures thereof.

22. The method of claim 21 wherein said sugar alcohol is sorbitol.

23. The method of claim 20 wherein said thymol is present in amounts of about 0.02 to about 0.1% by weight, said sugar alcohol is present in amounts of about 20 to about 55% by weight, and said anethole is present in amounts of about 0.01 to about 0.035% by weight, wherein said percents by weight are based on the total weight of the product.

24. The method of claim 20 wherein said sugar alcohol is present in amounts of abour 25 to about 50% by weight, said anethole is present in amounts of about 0.015 to about 0.025% by weight, and said thymol is present in amounts of about 0.05 to about 0.075%, said precents by weight being based on the weight of the product.

25. The method of claim 20 wherein said sugar alcohol is present in amounts of about 28 to about 32% by weight, said anethole is present in amounts of about 0.018 to about 0.022 percents by weight, and said thymol is present in amounts of about 0.06 to about 0.07% by weight, said % by weight being based on the weight of the product.

* * * * *